United States Patent [19]

Boissonneault et al.

[11] Patent Number: 5,208,225

[45] Date of Patent: May 4, 1993

[54] COMPOSITIONS CONTAINING FIXED COMBINATIONS

[75] Inventors: Roger M. Boissonneault, Long Valley; Henry A. Miller, Jr., Lake Hopatcong, both of N.J.

[73] Assignee: Warner-Lambert Company, Morris Plains, N.J.

[21] Appl. No.: 781,568

[22] Filed: Oct. 22, 1991

Related U.S. Application Data

[63] Continuation-in-part of Ser. No. 647,189, Jan. 24, 1991, abandoned, which is a continuation of Ser. No. 366,796, Jun. 15, 1989, abandoned, which is a continuation-in-part of Ser. No. 168,106, Mar. 14, 1988, abandoned, which is a continuation-in-part of Ser. No. 73,367, Jul. 6, 1987, abandoned, which is a continuation of Ser. No. 834,263, Feb. 26, 1986, abandoned.

[51] Int. Cl.$^5$ .......................................... A61K 31/56
[52] U.S. Cl. .................................. 514/178; 514/182; 514/843; 514/899
[58] Field of Search ............... 514/169, 170, 171, 178, 514/182, 843, 899

[56] References Cited

U.S. PATENT DOCUMENTS

| | | | |
|---|---|---|---|
| 3,836,651 | 9/1974 | Rudel et al. | 514/170 |
| 3,932,635 | 1/1976 | Segre | 514/170 |
| 3,969,502 | 7/1976 | Lachnit-Fixson | 514/170 |
| 4,291,028 | 9/1981 | Vorys | 514/178 |
| 4,292,315 | 9/1981 | Vorys | 514/178 |
| 4,315,925 | 2/1982 | Hussain et al. | 424/239 |
| 4,383,993 | 5/1983 | Hussain et al. | 424/239 |
| 4,390,531 | 6/1983 | Edgren | 514/178 |
| 4,425,339 | 1/1984 | Pitchford | 514/170 |
| 4,826,831 | 5/1989 | Plunkett et al. | 514/170 |
| 5,108,995 | 4/1992 | Casper | 514/170 |

FOREIGN PATENT DOCUMENTS 8431405 7/1985 Australia .
136011 3/1985 European Pat. Off. .

OTHER PUBLICATIONS

Abstract from "Abstracts of Current, Clinical and Basic Investigation" 35th Annual Clinical Meeting, Apr. 27-30, Las Vegas, Nev.
British Journal of Obstetrics and Gynecology, vol. 94, pp. 130-135, published Feb. 1987.
The Lancet, Oct. 12, 1985, by C. Christiansen, et al. p. 800, column 2.
Acta Obstet Gynecol Scand 63:673-677, (1984) by Mattsson, et al. (See p. 673, column 2 last paragraph).
Elsevier Biomedical Press (1982), article by L. A. Mattsson, et al., p. 95 (See p. 96, section entitled "Material and Methods".
The Medical Journal of Australia, 1974, pp. 688-690.
Acta Object Gynecol Scand Suppl 106:17-22, 1982.
Obstetrics & Gynecology, 1983, pp. 682-686.
Aust. N.Z.J. Obstet Gynaec., 1983, pp. 43-47.
Collection of chapters from "Hormone Therapy of the Menopause and Aging".
The Merck Index; 10th Ed. (1983); pp. 542, 960.

*Primary Examiner*—Frederick E. Waddell
*Assistant Examiner*—T. J. Criares
*Attorney, Agent, or Firm*—Ronald A. Daignault

[57] ABSTRACT

Continuous administration of compositions containing a fixed quantity of synthetic estrogen in combination with a synthetic progestogenic agent are useful to relieve menopausal symptoms, to prevent osteoporosis and for other hormone-replacement treatments. Also described is an improved manufacturing process for such compositions especially for low tablet dosage forms.

6 Claims, No Drawings

COMPOSITIONS CONTAINING FIXED COMBINATIONS

CROSS-REFERENCE TO RELATED APPLICATIONS

This application is a continuation-in-part of U.S. Ser. No. 647,189 of Jan. 24, 1991, now abandoned which is a continuation of U.S. Ser. No. 366,796 of Jun. 15, 1989, now abandoned, which is a continuation-in-part of U.S. Ser. No. 168,106 of Mar. 14, 1988, now abandoned, which is a continuation in-part of U.S. Ser. No. 073,367 of Jul. 6, 1987, now abandoned, which is a continuation of U.S. Ser. No. 834,263 of Feb. 26, 1986, now abandoned.

BACKGROUND

The treatment of menopausal symptoms such as flashing, osteoporosis and other symptoms associated with hormone deficiency is old. Typically, the known formulations for such treatment have contained natural estrogen or other estrogenic component(s) as the only hormonal ingredient. Known formulations were designed to treat symptoms rather than to replace the physiologic deficiency that results from dysfunctional ovaries. Also known formulations were marketed without adequate dose ranging and dosed in a cyclic fashion. The administration of estrogen in a cyclic fashion was an attempt to rest the endometrium from the continuous stimulation of estrogen. This practice is questionable in that the half-life of equine estrogens can be long (lipid soluble) and the patient never falls out of therapeutic range. As a result, despite cyclic administration, the replacement of estrogen with these types of formulations containing estrogen only has led to evidence of hyperstimulation of the endometrium and, in some cases, subsequent adenocarcinoma.

To minimize the potential for hyperstimulation, 5–14 days of progestional therapy has been included on a monthly basis to slough the endometrium. As a result, the patient experiences a monthly withdrawal bleed similar to the premenopausal state. Market research with physicians indicates that the nuisance of this cyclic bleeding is the single most important reason postmenopausal females refuse or discontinue therapy. Although progestins protect against hyperstimulation, they have been associated with a negative effect on blood lipids. As opposed to estrogen's positive effect on lipids, e.g., increase HDL/lower LDL, progestin's negative effect on lipids may compromise the cardioprotective state of the premenopausal female.

THE INVENTION

Applicant has discovered that a fixed combination of estrogenic and progestogenic agents gives relief from menopausal symptoms with minimal side effects. In one preferred embodiment, a composition containing a fixed dosage of ethinyl estradiol, —i.e., 0.001–0.05 mg— along with a fixed dosage of norethindrone acetate —i.e., 0.1–1.0 mg— yields, when administered in a continuous sequence, acceptable hormone levels in patients.

Thus, the invention is concerned with compositions and methods in which a formulation containing a fixed estrogen/progestin ratio is administered to female individuals with resultant relief from hot flashes, osteoporosis and other conditions associated with hormone deficiency.

The invention is also concerned with a new process for preparing fixed combinations of norethindrone acetate and ethinyl estradiol, especially useful for low tablet dosage forms where the ratio of norethindrone acetate may be from about 1:100 to about 1:1000 and ethinyl estradiol from about 1:2000 to about 1:100,000, the final tablet weight. The process employs a two-component drug dilution introduced onto tableting excipients.

ADVANTAGES

The compositions and processes of the invention have several advantages over those already known in the art. Principal among their advantages are:

1. The compositions contain fixed, i.e., constant or unitary, quantities of both the estrogenic and progestogenic agents. This simplifies manufacturing, storage, and packaging.
2. The use of a continuously dosed product minimizes patient compliance problems associated with an alternating sequence of dual therapies.
3. The administration of a single combination product containing fixed quantities of hormonal agents is psychologically beneficial. Also it has been demonstrated that low doses of this combination of hormones results in an atrophic state that obviates the troublesome side effect of monthly withdrawal bleeding.
4. Through the use of dose ranging the invention is designed to replace that which is physiologically lost rather than treat symptoms with supraphysiologic doses of estrogen and progestin. The result is a therapy that is associated with a relatively low incidence of side effects.
5. The invention has demonstrated efficacy similar to existing therapy (20 mcg, ethinyl estradiol), however, at one-fourth the total dose of estrogen. As a result the margin of safety (thromboembolism) has been expanded as measured by effects on clotting factors and angiotensin levels.
6. Ultra low doses of estrogen/progestin dosed in a schedule consistent with the postmenopausal state of endogenous hormone production offers protection against hot flashes, osteoporosis, endometrial hyperplasia, cyclic bleeding, and potentially replicates the cardioprotective state of the premenopausal female.
7. The use of the new and improved process for preparing low tablet dosage forms involving the combination of two drugs in one solution eliminates any error that may occur with distribution of one drug more than the other.
8. The new process also provides for processing to be carried out in one piece of equipment, e.g., a P-K solids processor, from blending to addition of lubricant thereby eliminating the need for transfer and drying.
9. Other aspects and advantages of the invention will be made apparent by the following description and claims.

DESCRIPTION OF THE INVENTION

The compositions and methods of the invention are based upon the use of a novel combination of synthetic estrogenic and progestogenic ingredients.

The compositions generally contain about 0.001 to 0.05 parts by weight, preferably about 0.001 to about 0.02 parts, or more preferably about 0.001 to 0.01 parts of the estrogenic ingredient and about 0.1 to about 1.0 parts by weight of the progestogenic ingredient.

Generally, the ratios by weight of progestogenic to estrogenic components in the inventive compositions will be from about 20:1 to about 200:1, preferably about 50:1 to about 200:1, and more preferably about 100:1 to about 200:1.

While milligrams are the preferred units of measurement, any scale can be used so long as the ratio of the active hormonal ingredients remains fixed and is appropriate to the weight ratios set out above. For example, in especially low tablet dosage forms, micrograms are often used as the units of measurement.

The estrogenic ingredient of the inventive compositions can be any suitable synthetic estrogen or functional equivalent thereof. While ethinyl estradiol is the preferred estrogenic substance, other useful substances include conjugated estrogens, estrone sulfate, beta estradiol, quinestrol, and the like. Mixtures are operable.

The progestogenic ingredient is generally a synthetic progestogen; however, natural progestins may be used. Useful progestogenic substances include medroxyprogesterone, medroxyprogesterone acetate, norgestrel, desogestrel, and the like. Norethindrone acetate is preferred. Mixtures are operable.

While it is preferred that the synthetic estrogen and progestin be the only pharmaceutically active ingredients in the compositions, the use of other drugs and/or otherwise beneficial substances in the instant compositions is contemplated.

The use of conventional pharmaceutical carriers is contemplated. Other excipients such as perfumes, colorants, stabilizers, fillers, and the like can be used as well.

The compositions of the invention can be administrated via a variety of routes. Any method or combination of method by which a continuous dosage form can be administered is operable. Oral dosage forms are preferred.

When oral dosage forms are employed, it is generally preferred that they be solid or semisolid. However, liquid compositions are contemplated.

One aspect of the invention involves the packaging of the compositions of the invention, in a solid dosage form, in a pill case or compact for continuous administration. Thus, a package similar to that sometimes used for dispensing contraceptive pills, tablets, and the like can be employed. Thus, the individual who is to ingest the subject composition merely takes the pills, tablets, and/or capsule in a daily regimen.

In general, any dosage form and packaging concept can be used in combination so long as the composition is administered at least once daily in a continuous sequence.

More preferred dosage forms for the above regimen are those compositions containing a fixed dosage of ethinyl estradiol, 1-20 micrograms (mcg), with a fixed dosage of norethindrone acetate, 0.1-1.0 milligrams (mg), wherein the ratio of norethindrone acetate to ethinyl estradiol is from about 50:1 to about 200:1. Most preferred contain a fixed dosage of 1-10 mcg ethinyl estradiol and 0.1-1.0 mg norethindrone acetate, wherein the ratio of norethindrone acetate to ethinyl estradiol is from about 100:1 to about 200:1.

Particularly valuable compositions contain as active ingredients:
1 mcg ethinyl estradiol and 0.2 mg norethindrone acetate;
2.5 mcg ethinyl estradiol and 0.5 mg norethindrone acetate;
5 mcg ethinyl estradiol and 1 mg norethindrone acetate, and
10 mcg ethinyl estradiol and 1 mg norethindrone acetate.

The compositions of the invention are useful for treating osteoporosis, hot flashes, withdrawal bleeding, and other disorders and symptoms generally associated with hormone deficiency, many of which are experienced during menopause.

Thus, for example, in a blinded, prospective, dose-response pilot study of continuous estrogen-progestin replacement therapy, 77 thin, nonsmoking, white women, who were 12 to 60 months postmenopausal and had normal medical histories, were randomly assigned to receive one of five dose combinations of daily ethinyl estradiol and norethindrone acetate (20 mcg and 1.0 mg, 10 mcg and 1.0 mg, 10 mcg and 0.5 mg, 5 mcg and 1.0 mg, and 5 mcg and 0.5 mg) or conjugated estrogens 0.625 mg on Days 1 to 25 and medroxyprogesterone acetate 10 mg on Days 16 to 25. An additional 10 women meeting the same criteria served as a comparison group by taking calcium only. During 12 months of therapy, continuous users had significantly less vaginal bleeding and spotting than did sequential users. As compared with baseline values, bone metabolism, and computerized tomographic measurements of vertebral trabecular bone density at Month 12 indicated reduced bone turnover and increased density in hormone users. Endometrial biopsy specimens were negative for hyperplasia and neoplasia. The continuous ethinyl estradiol-norethindrone acetate tablet, even at the lowest doses studied, provided the same salutary effects on bone, endometrium and postmenopausal symptoms as sequential therapy while minimizing annoying vaginal bleeding and spotting.

MATERIAL AND METHODS

Advertisements in Cleveland newspapers requested postmenopausal women to volunteer in a study of estrogen replacement. Approximately 150 respondents were screened by telephone interview according to these inclusion criteria: (1) 12 to 60 months had passed since natural menopause (time since last menstrual bleeding); (2) they were white or Oriental; (3) they were within 10% of ideal body weight for height and frame (Metropolitan Insurance Company standards); (4) they had not received hormonal therapy for the last 3 months; (5) they did not smoke; (6) their medical histories were negative for carcinoma, hypertension, diabetes, mellitus, disease of the liver, gallbladder disease, heart or vascular system diseases, alcoholism, and corticosteroid therapy. These criteria were designed to select a sample of women who were at risk for osteoporosis and were homogenous in factors related to metabolism of estrogen. Ninety-five women were eligible to participate in the study. These women were invited to undergo a thorough baseline evaluation, which included a history, physical examination, electrocardiogram, mammogram, endometrial biopsy, and routine blood chemistry tests. Eight other women were excluded; all of the remaining 87 women who met the inclusion criteria gave informed consent to participate in the study, as approved by the Investigational Review Board of the University Hospitals of Cleveland.

Rather than exclude the 10 women who did not wish to take hormones, we decided to administer calcium carbonate, 1000 mg daily (os-Cal 500 b.i.d., Marion Laboratories, Kansas City, Mo.), and undertake follow-up of these women. They formed a self-selected "calcium-only" group (Group A) and had the same demographic characteristics and medical surveillance as the other participants. Along with the 1000 mg daily dose of calcium carbonate, the remaining 77 women were randomly allocated to receive either sequential estrogen-progestin therapy or one of five dose combinations of continuous therapy (Table I). The latter six groups (B through G) constituted the principal focus of the study.

TABLE I

| Group | n | Treatment* |
|---|---|---|
| | Treatment Schedule | |
| A: Calcium only | 10 | No hormone replacement |
| B: Sequential | 12 | Conventional combination therapy: Conjugated equine estrogens 0.625 mg Days 1-25 and medroxyprogesterone acetate 10 mg Days 16-25 |
| C: 20/1 Continuous | 12 | Daily ethinyl estradiol 20 mcg and norethindrone acetate 1.0 mg |
| D: 10:1 Continuous | 14 | Daily ethinyl estradiol 10 mcg and norethindrone acetate 1.0 mg |
| E: 10/0.5 Continuous | 13 | Daily ethinyl estradiol 10 mcg and norethindrone acetate 0.5 mg |
| F: 5/1 Continuous | 14 | Daily ethinyl estradiol 5 mcg and norethindrone acetate 1.0 mg |
| G: 5/0.5 Continuous | 12 | Daily ethinyl estradiol 5 mcg and norethindrone acetate 0.5 mg |

*All patients received 1000 mg calcium carbonate daily
Participants who refused hormone therapy In the women receiving sequential therapy, the study could not be blinded because they were required to take two pills daily with a cyclic schedule (Group B). With continuous therapy (Groups C through G), women consumed a single tablet of ethinyl estradiol and norethindrone acetate. Although aware of membership in the continuous treatment group, participants and investigators were blinded to dose. Throughout the study, data excerpters and those performing laboratory and radiologic measurements remained completely blinded to group membership.

Data collection included a history, physical examination, electrocardiogram, mammography, and information on menopausal symptoms, endometrial histologic features, bone activity, and lipid metabolism. Baseline data were obtained (0 months of treatment), and thereafter measurements were done according to the schedule outlined in Table II.

TABLE II

| Study | Months of Therapy |
|---|---|
| Studies Done During the 12-Month Observation Period | |
| History, physical examination, and mammography | 0, 12 |
| Symptom analysis | |
| By diary | 1, 2 |
| By interview | 0, 2, 4, 6, 8, 10, 12 |
| Bone activity | |
| Bone Gla, alkaline phosphatase, calcium, phosphorus | 0, 1, 6, 12 |
| Urine sampling | 0, 1, 6, 12 |
| Quantitative computerized tomography of lumbar spine | 0, 12 |
| Lipid metabolism | |
| Total cholesterol, triglycerides, and lipid fractions | 0, 2, 6, 12 |

During the baseline interview, women reported duration of menopause, frequency of hot flushes (number per day), and incidences of vaginal bleeding and spotting. Participants were instructed to record their symptoms daily in a diary. After the first 2 months of treatment, data on menopausal symptoms were assessed by interview only.

Endometrial biopsies were performed by the investigators at 0 and 12 months with the women under paracervical block anesthesia, by Vabra suction curettage (Berkeley Medevices Inc., Berkeley, Calif.). Women randomized to sequential therapy underwent biopsy between Cycle Days 21 and 25. All tissue samples were fixed in formalin, labeled for blinding purposes, and then interpreted by attending pathologists of the University Hospitals of Cleveland.

At baseline and after 12 months of treatment, participants underwent quantitative computerized tomography of the trabecular portion of L1-3 vertebral bodies. A siemens DR3 system (Siemens AG, Iselin, N.J.) and the CIRS model 4 lumbar simulator (Computerized Imaging Reference Systems, Norfolk) were used. This phantom uses a solid resin reference plug rather than the liquid reference material used in the Genant phantom, making it less susceptible to variation over time. Hounsfield numbers were obtained and calcium hydroxyapatite content was calculated with the CIRS data graphic correlation. The scan technique used 96 kV and 150 mA. Values for L1, L2, and L3 were averaged, yielding a coefficient of variation of 1.5% to 2.0%.

Blood specimens for serum total cholesterol, low-density lipoprotein (LDL), high-density lipoprotein (HDL), very-low-density lipoprotein (VLDL), triglycerides, total alkaline phosphatase, phosphorus, and total calcium were collected by venipuncture the morning after an overnight fast, into Vacutainer serum separator tubes (Becton-Dickinson, Rutherford, N.J.). Plasma specimens for bone Gla protein (osteocalcin) were collected in citrated Vacutainer tubes. Plasma and serum were separated by centrifugation after 30 minutes was allowed for clotting. The serum alkaline phosphatase, phosphorus, and total calcium assays were performed the morning of collection with the sequential Multiple Analyzer with Computer (SMAC) system (Technicon Corporation, Tarrytown, N.Y.). Total cholesterol was estimated by the SMAC Liebemann-Burchard reaction and triglycerides by the SMAC lipase method. HDL cholesterol was precipitated by magnesium and dextran, then assayed in the CoBas Bio centrifugal analyzer (Roche Diagnostics, Nutley, N.J.). LDL cholesterol was calculated by the formula: LDL=Total cholesterol−HDL−Triglycerides/6.25.

Plasma for Gla protein analysis was frozen at −70° C. and stored until completion of the study, when it was measured by Dr. C. Christiansen in Denmark, utilizing a radioimmunoassay with an antibody raised in rabbits to calf bone Gla protein. Urine samples were collected the morning after an overnight fast and after 48 hours of avoidance of gelatins and soups. Participants were instructed to void 2 hours before the appointment, drink approximately 24 ounces of tap water, then collect the urine specimen at our office. Assays for urinary calcium and creatinine were performed the morning of collection, while aliquots for measurement of hydroxyproline were frozen at $-30°$ C and stored until the end of the study. Urinary creatinine was assayed by a colorimetric method that used the Jaffe reaction of a CoBas Bio centrifugal analyzer. The urinary calcium level was determined by the Hitachi 705 calcium method. Urinary hydroxyproline assays were run at the completion of the study using a cation exchange resin and a colorimetric method.

Where appropriate, data was transformed to more closely fit a Gaussian distribution. Statistical analyses used were Student's t-test, analysis of variance, analysis of covariance, and Fisher's exact test. Within-group changes were studied both by repeated measures of analysis of variance and by transformation to percent change over time.

RESULTS

All 87 women who participated in the study were white with a mean age of 52.8 years, mean weight of 135.1 pounds, and mean height of 64.6 inches (Table III).

the withdrawal at 1 month of a woman receiving the combination 20/1 (Group C). A venogram for this participant was negative for deep venous thrombosis. Three women receiving sequential treatment (Group B, at 3, 6, and 7 months of treatment) and one woman receiving combination 5/1 (Group F, at 1 month of therapy) withdrew from the study because of vaginal bleeding. Other reasons cited for withdrawal were constipation (two combination 5/1 (Group F) users after 1 and 2 months), nausea (one sequential, Group B user after 1 month), depression (one combination 10/1, Group D user after 2 months), viral pneumonia (one combination 5/0.5, Group G user after 3 months), cholelithiasis (one combination 10/0.5, Group E user after 11 months), and being tired of participation (one combination 5/1, Group F user after 3 months). After withdrawals were excluded, the various groups remained similar in demographics (age, weight, height), in duration since menopause, and in their experience of hot flushes. For the findings reported, Table III, dropouts were excluded from analyses.

The average number of hot flushes per week declined over time. Although the calcium-only group demonstrated a decline, this was not statistically significant, in contrast to the decline noted with all hormonal treatment groups. The groups differed, however, in their rate of decline of hot flushes. Women using a continuous estrogen-progestin regimen (Groups C through G) had an earlier reduction in their frequency of hot flushes when compared with women using the conventional sequential estrogen-progestin program (Group B).

TABLE III

| Summary of Patient Characteristics | | | | | | | | |
|---|---|---|---|---|---|---|---|---|
| | Group A (n = 10) | Group B (n = 12) | Group C (n = 12) | Group D (n = 14) | Group E (n = 13) | Group F (n = 14) | Group G (n = 12) | Overall (n = 87) |
| Age | | | | | | | | |
| Mean | 53.8 | 53.1 | 52.0 | 52.0 | 53.6 | 52.4 | 52.8 | 52.8 |
| Range | 50–57 | 48–58 | 47–57 | 37–58 | 47–58 | 48–59 | 42–58 | 37–59 |
| Weight (lb) | | | | | | | | |
| Mean | 132.6 | 130.7 | 136.3 | 140.9 | 136.0 | 131.9 | 136.7 | 135.1 |
| Range | 121–150 | 106–154 | 112–164 | 103–165 | 103–171 | 96–169 | 112–163 | 96–171 |
| Height (in) | | | | | | | | |
| Mean | 63.8 | 64.7 | 64.7 | 65.4 | 65.0 | 63.7 | 65.0 | 64.6 |
| Range | 61–65 | 60–68 | 59–69 | 61–68 | 62–68 | 55–69 | 60–68 | 55–69 |
| Postmenopausal duration (mo) | | | | | | | | |
| Mean | 31.1 | 28.1 | 27.9 | 28.4 | 37.8 | 33.9 | 36.2 | 32.0 |
| Range | 16–51 | 12–59 | 15–53 | 13–45 | 15–59 | 16–54 | 12–59 | 12–59 |
| Hot flushes (No./day) | | | | | | | | |
| Mean | 3.0 | 7.1 | 8.9 | 5.6 | 8.4 | 7.3 | 5.6 | 6.6 |
| Range | 0–5 | 1–15 | 0–20 | 1–20 | 0–12 | 1–25 | 1–16 | 0–25 |
| Duration (mo) | | | | | | | | |
| Mean | 41.3 | 31.8 | 21.8 | 36.6 | 36.3 | 48.1 | 48.8 | 38.0 |
| Range | 2–105 | 12–92 | 7–45 | 2–188 | 6–59 | 7–117 | 1–116 | 1–188 |
| Drop outs (n) | 0 | 4 | 1 | 1 | 2 | 4 | 1 | 13 |

The average postmenopausal duration was 32 months, with an average of 6.8 hot flushes per day experienced over an average of 38 months. There were no statistically significant differences among groups in duration since menopause before study entry, number of hot flushes, duration of hot flushes, diet, or level of exercise.

Thirteen women dropped out over the 12-month observation period (Table III). The screening mammogram for one participant receiving the combination 10/0.5 (Group E) was read as suspicious. Before study entry, a surgical consultation was obtained. A 3-month follow-up mammogram was recommended and subsequently led to needle biopsy that revealed carcinoma in situ. A diagnosis of superficial thrombophlebitis led to Compared with women who received only calcium (Group A), women receiving sequential estrogen-progestin (Group B) did not achieve a statistically significant ($p<0.05$) suppression of hot flushes until 8 months of treatment, while the women on a regimen of continuous therapy showed a significant reduction ($p<0.05$) by the second month of treatment. The variation around the mean was minimal and similar in all groups. Reduction in frequency of hot flushes was accompanied by improvements in vaginal dryness, dyspareunia, depression, insomnia, and fatigue. The number of women initially reporting these symptoms, however, was insufficient to perform statistical analyses for comparison among groups.

All treatment groups reported vaginal bleeding (defined as enough bleeding to necessitate use of tampons or pads) and spotting (bleeding not necessitating sanitary protection) in the early months of therapy. As mentioned above, three sequential users (Group B) withdrew because of vaginal bleeding, and after 12 months all eight remaining sequential users were still reporting vaginal bleeding and spotting. Only one continuous user withdrew because of vaginal bleeding; after 12 months none of the continuous users was bleeding and only four of 56 were reported spotting. After 12 months the difference in bleeding and spotting between sequential and continuous users was significant by Fisher's exact test ($p<10^6$). Furthermore, the spotting reported by continuous users varied across the groups and thus was not related to dose.

The endometrial biopsy specimens revealed no cases of hyperplasia or neoplasia. At 12 months four sequential users had secretory endometrium and one sequential user had mixed secretory-proliferative activity. The remaining three sequential users had inactive endometrium or insufficient tissue for diagnosis. One continuous user had secretory endometrium (combination 20/1) while 43 continuous users had inactive endometrium or insufficient tissue for diagnosis. Three women in the continuous therapy groups (one each in Groups C, D, and E) were found to have endometrial polyps in the 12-month biopsy specimens, although none was found in the screening biopsy specimens. Histologically, both stromal and glandular elements of the polyps were benign in appearance. Only one of the three women with endometrial polyps (Group C) reported vaginal spotting. A total of 18 subjects did not undergo screening biopsy because we were unable to pass a uterine sound. For the same reason 12 of these women could not undergo biopsy at the end of the observation period. These subjects were evenly distributed among the treatment groups.

At baseline, there were no differences among the groups in bone density ($p=0.61$). After 12 months, the bone densities of the women taking calcium only (Group A) remained unchanged ($p=0.47$). Use of estrogen-progestin, regardless of the regimen, in contrast to calcium only, was associated with an increase in bone density ($p=0.005$). All doses of continuous combination therapy, even the lowest combination dose of 5/0.5 (Group g), produced a significant gain in bone density ($p=0.001$). The gain in bone density corresponded directly with the dose of estrogen; however, analysis of the dose-response relationship was limited by the small sample sizes. The increase in bone density and tendency for a dose-response relationship was replicated in analysis of covariance, adjusting for baseline bone density and for duration since menopause.

There were no differences among groups in baseline values for serum phosphorus, serum alkaline phosphatase, bone Gla protein, urinary calcium/creatinine ratio, or hydroxyproline/creatinine ratio. For serum calcium Group A (calcium only) had a lower baseline level than the baseline values for estrogen-progestin users ($p=0.033$). After 12 months the serum calcium level increased significantly in Group A ($p=0.043$) but did not change over time for the sequential ($p=0.69$) and continuous ($p=0.40$) estrogen-progestin users. At 12 months there were no group differences ($p=0.26$). Serum phosphorus values decreased from baseline in women receiving continuous therapy ($p=0.0001$) but not in those women receiving sequential ($p=0.91$) or calcium-only ($p=0.33$) treatment. The continuous users differed from both sequential users ($p=0.042$) and calcium-only users ($p=0.001$) in magnitude of change from the baseline. Bone Gla protein and serum alkaline phosphatase did not change from baseline values for the calcium only users ($p=0.98$ and $p=0.28$, respectively), but both decreased significantly in all estrogen-progestin groups ($p=0.0001$). The decline in Gla protein (about 66% from baseline) and in alkaline phosphatase (about 9.6% from baseline) was the same for sequential therapy as for continuous estrogen-progestin treatment ($p=0.76$ and $p=0.96$, respectively). All groups experienced a decline in urinary hydroxyproline/creatinine ratio ($p<0.05$), and there were no differences between calcium-only (Group a) users and hormone users (Groups B through G). The urinary calcium/creatinine ratio analysis yielded inconsistent results. At baseline, the continuous therapy and calcium-only groups did not differ in either total cholesterol ($p=0.41$) or LDL-cholesterol ($p=0.83$). Compared with the calcium-only group and continuous estrogen-progestin users, the sequential estrogen-progestin users, the sequential estrogen-progestin users had both significantly lower total cholesterol ($p=0.014$) and significantly lower LDL-cholesterol ($p=0.025$). There were no group differences, at baseline, for HDL-cholesterol ($p=0.88$) or triglycerides ($p=0.14$). After 12 months the calcium-only group showed an increase in total cholesterol ($p=0.003$) and LDL-cholesterol ($p=0.011$) but no change in HDL-cholesterol ($p=0.45$) or triglycerides ($p=0.46$) (Table IV).

TABLE IV

| | Mean Lipid Values After 12 Months of Treatment | | |
|---|---|---|---|
| | Calcium Only (Group A) | Sequential (Group B) | Continuous (Groups C–G) |
| Total cholesterol Baseline value (mg/dl) | 214.2 | 198.4 | 227.6 |
| % Change | 12.3 | 12.7 | −3.0 |
| p Value | 0.003 | 0.061 | 0.072 |
| HDL-cholesterol Baseline value (mg/dl) | 66.2 | 65.3 | 66.3 |
| % Change | 0.5 | −0.2 | −0.8 |
| p Value | 0.45 | 0.89 | 0.13 |
| LDL-cholesterol Baseline value (mg/dl) | 132.7 | 112.8 | 135.4 |
| % Change | 3.1 | 3.2 | −0.4 |
| p Value | 0.011 | 0.093 | 0.51 |
| Triglyceride Baseline value (mg/dl) | 76.7 | 80.1 | 110.4 |
| % Change | 2.2 | 8.3 | 2.0 |
| p Value | 0.46 | 0.0001 | 0.12 |

The sequential estrogen progestin users tended toward an increase in total cholesterol ($p=0.061$), LDL-cholesterol ($p=0.093$), and triglycerides ($p=0.001$), but HDL cholesterol remained the same ($p=0.89$). In contrast, the continuous users tended toward a decrease in total cholesterol ($p=0.072$), while HDL-cholesterol ($p=0.13$), LDL-cholesterol ($p=0.51$), and triglycerides ($p=0.12$) remained without significant change. The changes in total cholesterol and LDL-cholesterol experienced by the continuous users differed from those experienced by the sequential estrogen-progestin users ($p=0.019$ and $p=0.029$, respectively); group differences in HDL-cholesterol (p=0.19) and triglycerides (p=0.09) were not significant.

There were no significant changes or group differences observed in blood pressure or body weight. In addition, there were no clinically significant effects on the hematopoietic system, electrolytes, renal function, fasting blood glucose, mammography, or Papanicolaou smear.

In summary, it was found that continuous ethinyl estradiol and norethindrone acetate are effective for improving postmenopausal bone metabolism and reducing symptoms of the postmenopausal period with significantly less annoying vaginal bleeding. These effects were found even at the lowest doses studied and occurred without adverse effects on lipid metabolism.

The lowest dose tablet used in the study was effective in increasing bone density. The minimal dose of ethinyl estradiol required to improve bone metabolism previously had been established at 20 mcg. It was found that combination with norethindrone acetate lowers the threshold to at least 5 mcg.

Lipid metabolism in the women after 12 months of sequential estrogen-progestin therapy was similar to the lipid changes in women receiving calcium only; levels of both total cholesterol and LDL-cholesterol increased. In contrast, after 12 months of continuous estrogen-progestin therapy women had lower total cholesterol with LDL-cholesterol remaining at baseline. The women who participated in the study had higher HDL-cholesterol levels (mean 66.7 mg/dl) and lower total cholesterol levels (mean 221.9 mg/dl) than the mean levels at the 50th percentile reported for white women at ages 55 to 64 (60 and 244 mg/dl, respectively). A common statistical phenomenon, called regression toward the mean, may partially explain the results. Women who had lipid values most extreme from the "norm" at baseline were likely to have repeat values move in the direction of the norm. It has also been noted that measures of lipid metabolism lack sufficient sensitivity to detect small changes over time.

The full report of the above described clinical study is in Am J Obstet Gynecol 1990; 162:438-46.

The present invention includes combinations of synthetic estrogens and synthetic progestogens and is not limited to the combination and continuous administration of ethinyl estradiol and norethindrone acetate. For example, continuous administration of a combination of conjugated equine estrogen and medroxyprogesterone acetate is described in Obstet Gynecol 1988;71:39. Continuous administration of 17β-estradiol and norethindrone acetate is described in Brit J Obstet and Gynecol 1990;97:1087-1092. Thus, combinations of estrogens and progestogens at the fixed ratio and dosage of the present invention and administration of such in a continuous sequence provides relief of menopausal symptoms. The fixed compositions of the present invention can be prepared by an improved process adaptable as well for ultra low dose formulations which comprise dissolving together in one vessel both the estrogenic and progestogenic ingredients, e.g., norethindrone acetate and ethinyl estradiol in alcohol; plating the solution of ingredients onto a mixture of lactose and excipients, removing the alcohol by drying, adding incrementally other excipients, and blending in a lubricant, e.g., calcium stearate, and compressing the resulting mixture into tablets.

The process may be illustrated by the following scheme:

---

BLENDING SCHEME FOR TWO COMPONENT DRUG DILUTION USED IN NORETHINDRONE ACETATE/ETHINYL ESTRADIOL TABLET GRANULATION BLENDED IN P-K LIQUID/SOLIDS BLENDER WITH INTENSIFIER BAR

A.
ETHINYL ESTRADIOL
NORETHINDRONE ACETATE
ALCOHOL SD 3A*
DISSOLVE ETHINYL ESTRADIOL AND NORETHINDRONE ACETATE IN SD 3A ALCOHOL WITH GENTLE STIRRING.

B.
LACTOSE FAST FLO
TWO COMPONENT DRUG SOLUTION
ADD "A" TO "B" IN P-K BLENDER WITH INTENSIFIER BAR AND BLENDER ON.
RINSE WITH ADDITIONAL ALCOHOL (20 ml/1 kg.). BLEND WITH INTENSIFIER BAR FOR 5 MINUTES. REMOVE AND DRY UNTIL ALL ALCOHOL IS EVAPORATED. SCREEN THROUGH A #30 SCREEN

C.
DRUG GRANULATION
MICROCRYSTALLINE CELLULOSE
STARCH CORN NF
ADD MICROCRYSTALLINE CELLULOSE WITH STARCH AND BLEND FOR MINUTES WITH INTENSIFIER BAR.

D.
DRUG GRANULATION
MICROCRYSTALLINE CELLULOSE
STARCH CORN NF
CALCIUM STEARATE
ADD CALCIUM STEARATE AND BLEND FOR 1 MINUTE WITH INTENSIFIER BAR AND 1 MINUTE WITHOUT INTENSIFIER BAR.

---

*Alcohol SD 3A = Denatured anhydrous ethanol 100 parts with 5 parts methanol. Drying may also be carried out under vacuum in this equipment.

The invention is illustrated by the following example(s).

EXAMPLE 1

1.00 g ethinyl estradiol U.S.P., (0.5% dilution, 5% excess) was combined with 0.5 g norethindrone acetate U.S.P. 8.66 g Hydrous Fast Flo lactose U.S.P. and 7.00 g corn starch N.F. in a suitable liquids/solids PK blender equipped with intensifier bar. The ingredients were blended for five minutes. All mixing was done using the intensifier bar unless specified otherwise.

17.50 g microcrystalline cellulose NF Powder was added to the resultant blend and mixed for 5 minutes. 34.64 g Hydrous Fast Flo lactose U.S.P. was added and all ingredients were blended for five minutes.

Thereafter, 0.70 g calcium stearate NF powder was added and blended with the intensifier bar for one minute and without it for one minute.

The final mixture was compressed 70 mg on 7/32 FFBE punches at 4-6 kg hardness and about 0.085 inch gauge. One thousand tablets were produced from the composition.

EXAMPLES 2-4

Using the same procedure described above, tablets were produced using the following ingredients:

| Ingredient | Ex. 2 | Ex. 3 | Ex. 4 |
|---|---|---|---|
| Ethinyl estradiol, U.S.P. (0.5% dilution, w/5% excess) | 2.00 | 1.00 | 2.00 |
| Norethindrone acetate, U.S.P. | 0.50 | 1.00 | 1.00 |
| Lactose, Hydrous Fast Flo, U.S.P. | | | |
| Initial Quantity: | 8.46 | 8.56 | 8.36 |

-continued

| Ingredient | Ex. 2 | Ex. 3 | Ex. 4 |
|---|---|---|---|
| Added Quantity | 33.84 | 34.24 | 33.44 |
| Corn Starch, NF | 7.00 | 7.00 | 7.00 |
| Microcrystalline cellulose | 17.50 | 17.50 | 17.50 |
| Calcium stearate | 0.70 | 0.70 | 0.70 |

EXAMPLE 5

| Each Tablet | | Ingredients | Per 1000 Tablets |
|---|---|---|---|
| 1.0 mcg | 1. | Ethinyl Estradiol U.S.P. | 0.001 g |
| 100.0 mcg | 2. | Norethindrone Acetate U.S.P. | 0.100 g |
| | 3. | Alcohol SD 3A Anhydrous q.s. | 10.000 ml |
| | 4. | Lactose USP Hydrous (Fast Flo) q.s. | 68.833 g |
| | 5. | Starch Corn NF q.s. | 10.000 g |
| | 6. | Cellulose Microcrystalline NF Granular (PH-102) q.s. | 20.000 g |
| | 7. | F.D. & C. Blue #1 Lake HT 31% q.s. | 0.066 g |
| | 8. | Calcium Stearate NF q.s. | 1.000 g |
| 100.000 mg | | To make | 100.000 g |

Component 7 was added to components 4 and 5 and blended in a suitable size P-K liquid/solids blender with intensifier bar for five minutes. Component 6 was then added and blended with intensifier bar for another five minutes.

In a separate container, components 1 and 2, the active ingredients, were dissolved in alcohol, component 3, and then added to the blender at a sufficient rate through intensifier bar with bar and blender on. The blender was rinsed with additional alcohol, 3, (20 ml/1 kg) through intensifier bar with blender and bar on. The entire mixture was blended an additional five minutes.

The damp granulated material was removed from the blender and air dried until all the alcohol evaporated, or preferably vacuum dried. The material was then re-blended with intensifier bar for five minutes. Component 8 was added and blended with intensifier bar for one minute and without for one minute.

The final mixture was compressed 100 mg on 0.208"×0.250 Oval punches at 6–9 kg units hardness and about 0.130" thickness. One thousand tablets were produced from the composition.

I claim:

1. A method for treating menopausal symptoms associated with hormone deficiency in a postmenopausal female host comprising continuous, daily administration to said host of a fixed combination in the form of a pharmaceutical composition for oral administration comprising:
   (a) about 1–20 mcg ethinyl estradiol, and
   (b) about 0.1–1.0 mg norethindrone acetate, wherein the ratio of norethindrone acetate to ethinyl estradiol is about 50:1 to about 200:1.

2. The method of claim 1, wherein the composition comprises:
   (a) 1–10 mcg ethinyl estradiol, and
   (b) 0.1–1 mg norethindrone acetate, wherein the ratio of norethindrone acetate to ethinyl estradiol is about 100:1 to about 200:1.

3. The method of claim 2, wherein the composition comprises 1 mcg ethinyl estradiol and 0.2 mg norethindrone acetate.

4. The method of claim 2, wherein the composition comprises 2.5 mcg ethinyl estradiol and 0.5 mg norethindrone acetate.

5. The method of claim 2, wherein the composition comprises 5 mcg ethinyl estradiol and 1 mg norethindrone acetate.

6. The method of claim 2, wherein the composition comprises 10 mcg ethinyl estradiol and 1 mg norethindrone acetate.

* * * * *